US 9,168,041 B2

(12) United States Patent
Zaritsky et al.

(10) Patent No.: US 9,168,041 B2
(45) Date of Patent: Oct. 27, 2015

(54) PEDIATRIC ESOPHAGEAL ATRESIA MAGNETIC ANASTOMOSIS SYSTEM

(71) Applicant: Cook Medical Technologies LLC, Bloomington, IN (US)

(72) Inventors: Mario Zaritsky, Chicago, IL (US); Andrés Aguirre, Chicago, IL (US)

(73) Assignee: Cook Medical Technologies LLC, Bloomington, IN (US)

( * ) Notice: Subject to any disclaimer, the term of this patent is extended or adjusted under 35 U.S.C. 154(b) by 212 days.

(21) Appl. No.: 13/773,213

(22) Filed: Feb. 21, 2013

(65) Prior Publication Data
US 2013/0226205 A1    Aug. 29, 2013

Related U.S. Application Data

(60) Provisional application No. 61/602,263, filed on Feb. 23, 2012.

(51) Int. Cl.
*A61B 17/11* (2006.01)
*A61B 17/00* (2006.01)
*A61B 19/00* (2006.01)

(52) U.S. Cl.
CPC ............. *A61B 17/11* (2013.01); *A61B 17/1114* (2013.01); *A61B 2017/00876* (2013.01); *A61B 2017/1132* (2013.01); *A61B 2019/2253* (2013.01)

(58) Field of Classification Search
CPC ................... A61B 17/1114; A61B 2017/1117; A61B 2017/1132; A61B 2017/1135; A61B 2017/1139; A61B 2017/1107; A61B 17/11
See application file for complete search history.

(56) References Cited

U.S. PATENT DOCUMENTS

| 2,308,484 | A | 1/1943 | Auzin et al. |
| 3,771,526 | A | 11/1973 | Rudie |
| 3,986,493 | A | 10/1976 | Hendren, III |
| 4,294,362 | A | 10/1981 | Martensson |
| 4,619,247 | A | 10/1986 | Inoue et al. |
| 4,873,977 | A | 10/1989 | Avant et al. |
| 4,978,323 | A | 12/1990 | Freedman |
| 5,429,131 | A | 7/1995 | Scheinman et al. |

(Continued)

OTHER PUBLICATIONS

International Search Report mailed May 29, 2013 for International Application No. PCT/US2013/025821.

(Continued)

*Primary Examiner* — Thomas McEvoy
(74) *Attorney, Agent, or Firm* — Brinks Gilson & Lione

(57) ABSTRACT

A system and a method for joining an upper and lower esophageal sacs in an infant are provided. The system includes a first elongate member having a first magnet, the first magnet including an end portion configured to abut an interior surface of the upper esophageal sac. The system also includes a second elongate member having a second magnet, the second magnet including an end portion configured to abut an interior surface of the lower esophageal sac. The system further includes a third elongate member having a third magnet and a spacer positioned distal to the third magnet. The third elongate member is positionable in the upper esophageal sac after the first elongate member has been removed. A magnetic force between the first magnet and the second magnet is configured to pull the first magnet and the second magnet towards each other to lengthen the upper and lower esophageal sacs.

20 Claims, 7 Drawing Sheets

(56) References Cited

U.S. PATENT DOCUMENTS

| | | |
|---|---|---|
| 5,681,260 A | 10/1997 | Ueda et al. |
| 5,690,656 A | 11/1997 | Cope et al. |
| 6,352,543 B1 | 3/2002 | Cole |
| 6,985,776 B2 | 1/2006 | Kane et al. |
| 7,282,057 B2 | 10/2007 | Surti et al. |
| 2003/0130610 A1 | 7/2003 | Mager et al. |
| 2003/0139703 A1 | 7/2003 | Burkett et al. |
| 2004/0034377 A1 | 2/2004 | Sharkawy et al. |
| 2005/0228412 A1* | 10/2005 | Surti ............................ 606/153 |
| 2006/0282106 A1* | 12/2006 | Cole et al. ..................... 606/153 |
| 2007/0276378 A1* | 11/2007 | Harrison et al. ................ 606/61 |

OTHER PUBLICATIONS

Written Opinion of the International Searching Authority mailed May 29, 2013 for International Application No. PCT/US2013/025821.

* cited by examiner

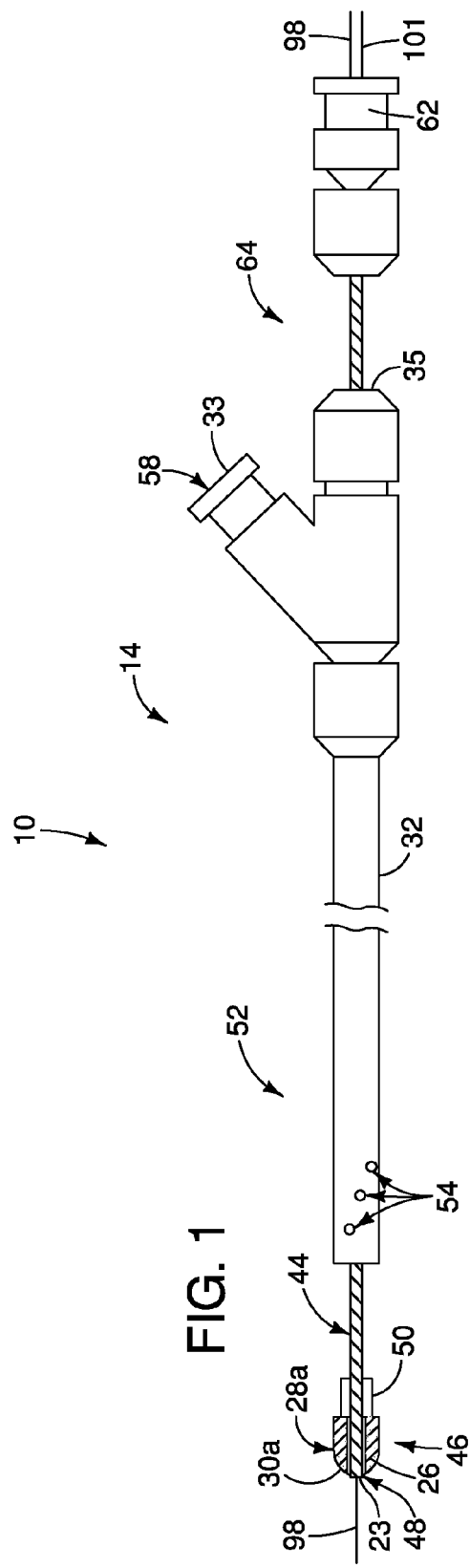

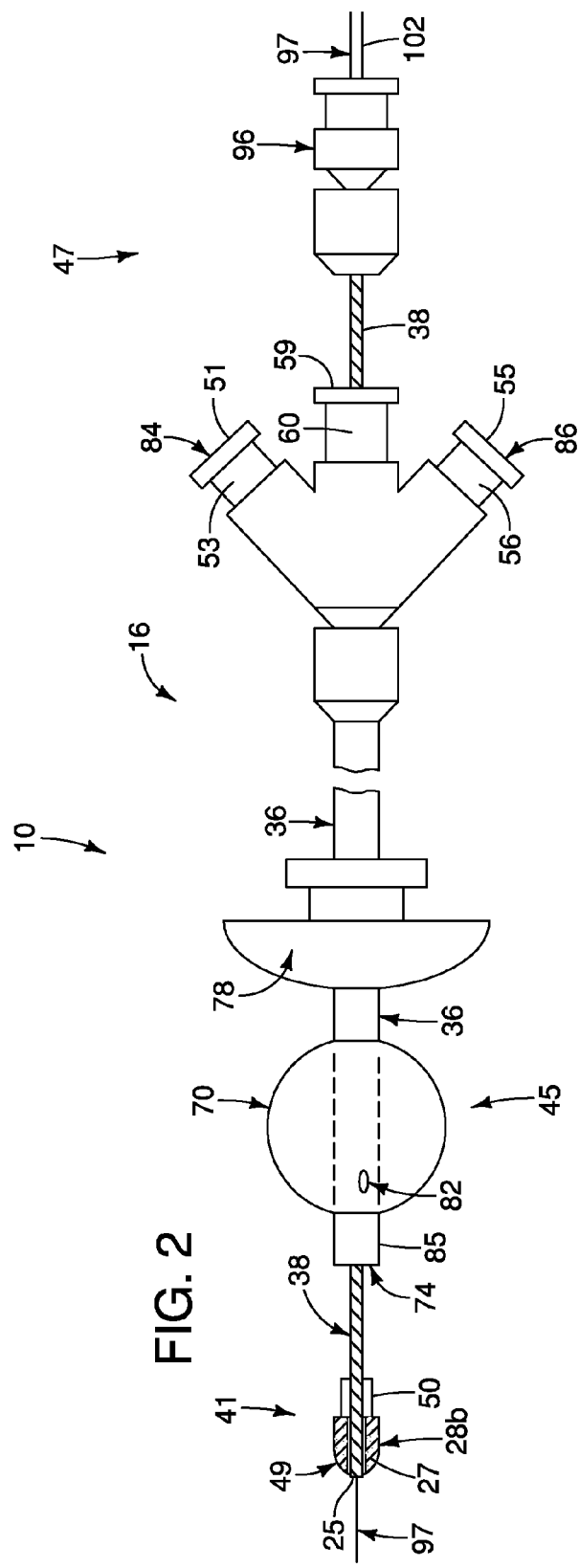

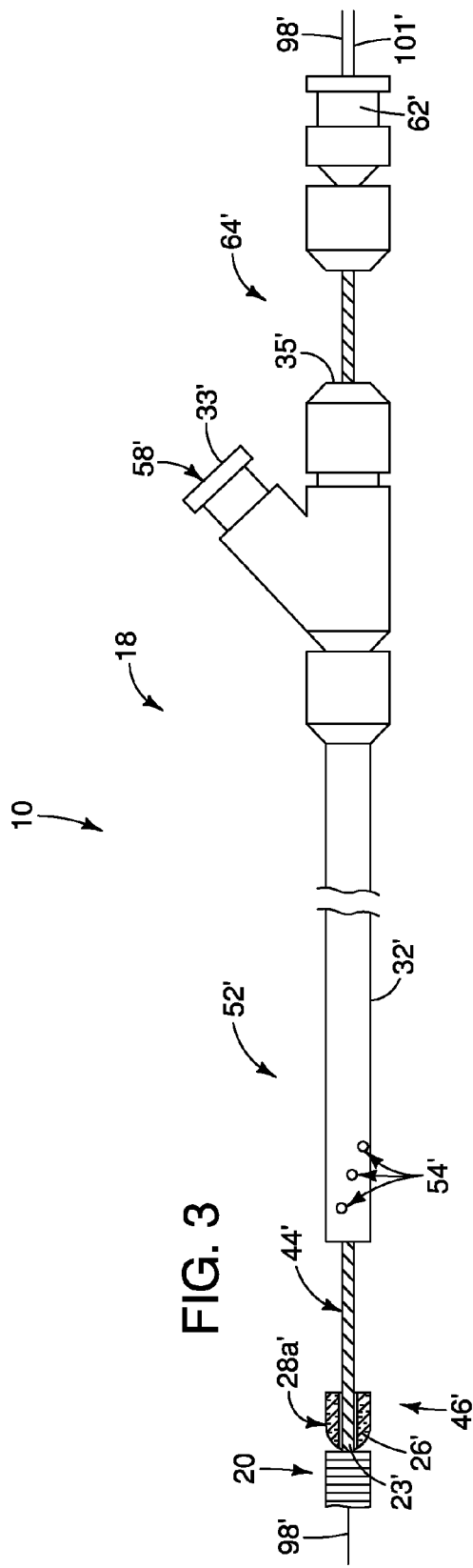

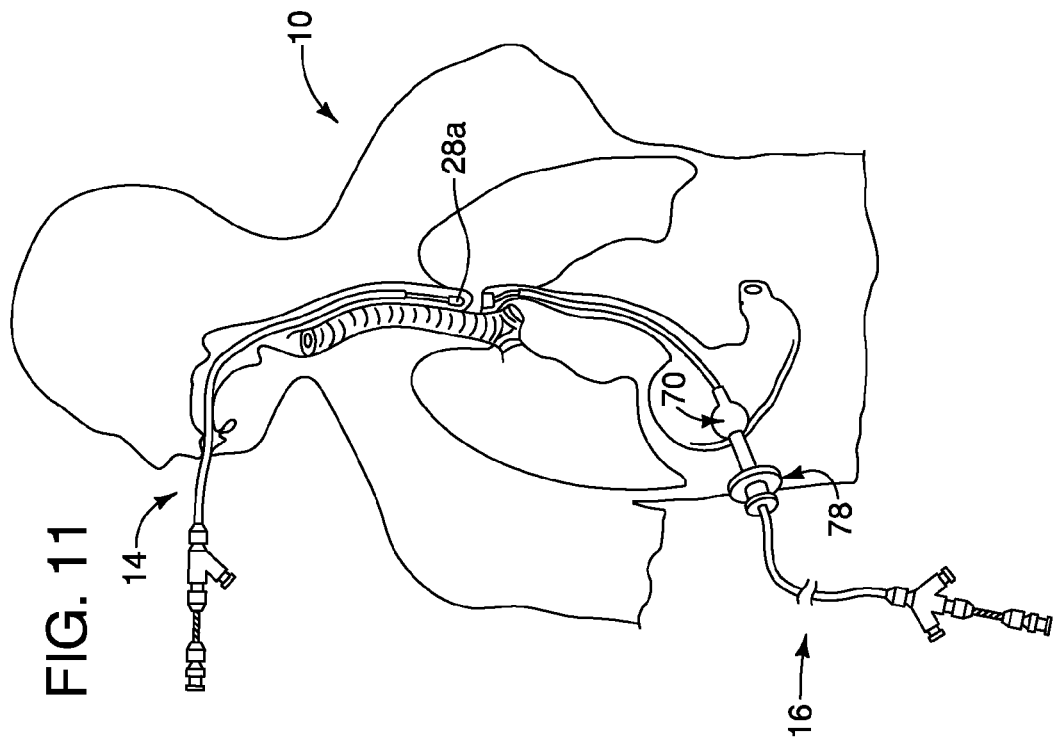
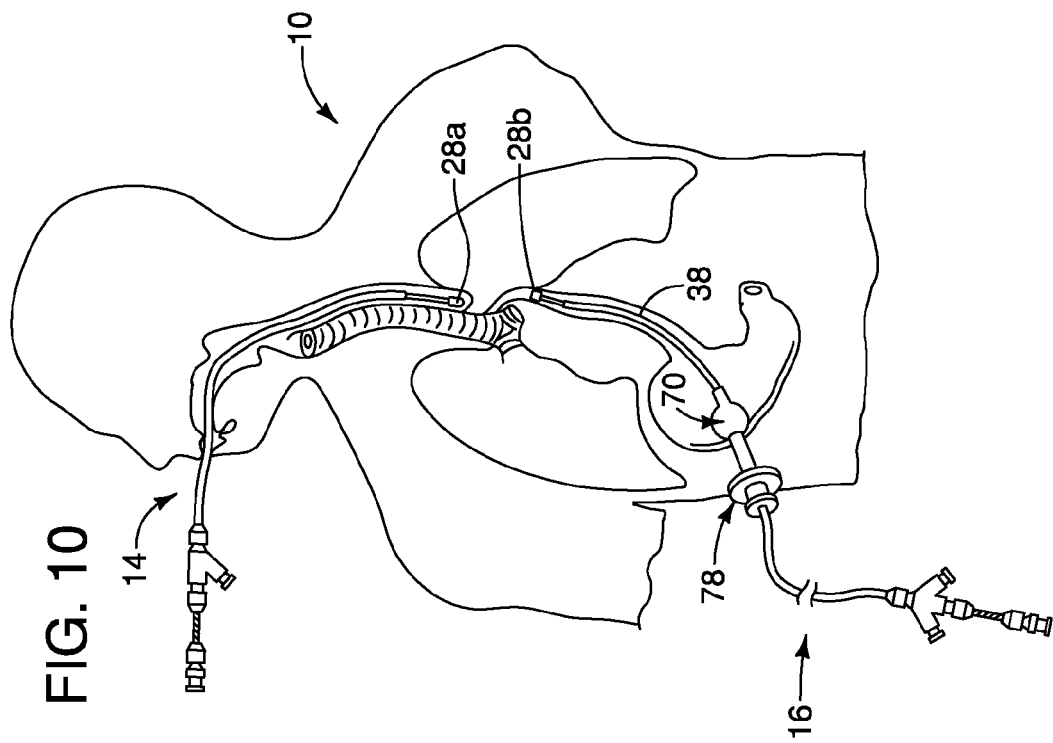

PEDIATRIC ESOPHAGEAL ATRESIA MAGNETIC ANASTOMOSIS SYSTEM

RELATED APPLICATIONS

This application claims the benefit of U.S. Provisional Application No. 61/602,263, filed Feb. 23, 2012, which is incorporated by reference herein in its entirety.

FIELD OF THE INVENTION

This invention relates to medical devices, and more particularly, to a method and device for non-surgically treating pediatric esophageal atresia.

BACKGROUND OF THE INVENTION

Esophageal atresia is a serious birth defect in which the esophagus, the long tube connecting the mouth to the stomach, is segmented and does not form a continuous passageway into the stomach. In particular, infants suffering from esophageal atresia are born with separate upper and lower esophageal portions (commonly referred to as esophageal sacs). In most forms of esophageal atresia the upper esophageal sac begins to fill with mucus and saliva shortly after birth. Consequently, excessive drooling, choking, and coughing are symptomatic of esophageal atresia. Moreover, an infant afflicted with this disorder instantaneously returns (i.e., expels) what he or she is fed, thereby preventing the digestion and absorption of orally administered foods.

There are several types of esophageal atresia. In one type of esophageal atresia, the upper and lower esophageal sacs are not attached to the trachea. That is, the lower esophageal sac does not develop an esophagotracheal fistula. In another type of esophageal atresia, the upper esophageal portion ends as a blind sac, whereas the lower esophageal portion is connected to the trachea by a narrow canal at a point just above the tracheal bifurcation. In yet another type of esophageal atresia, the narrow canal between the trachea and the distal portion of the esophagus forms a ligamentous cord. In rare instances, both the proximal and distal portions of the esophagus actually open into the trachea.

For a period of about three months after birth, the esophageal sacs spontaneously undergo a period of rapid growth toward each other. A number of different techniques have been used during this spontaneous growth period to achieve a more rapid approximation of the esophageal sacs. These techniques have included, for example, the use of a large external electromagnet, surgical techniques, and internally positioned magnets.

One such technique is described in detail in U.S. Pat. No. 3,986,493 (hereinafter "the '493 patent"), titled "Electromagnetic Bougienage Method" uses an external annular electromagnet to intermittently magnetize bougies located within each esophageal sac to lengthen the esophageal sacs and eventually surgically join the esophageal sacs.

Yet another method of treating esophageal atresia involves surgically applying sutures to the opposing ends of the esophageal sacs. The sutures create traction forces to the ends of the esophageal sacs during the rapid growth period, thereby causing further elongation of the esophageal sacs. Ultimately, the sutures cause the esophageal sacs to grow together.

Another method of treating esophageal atresia involves positioning a pair of catheters, each catheter having a magnetic tip as disclosed in U.S. Pat. No. 7,282,057. The magnetic forces created by both magnets results in approximation of the esophageal sacs.

The above-described conventional methods of correcting esophageal atresia present several drawbacks. The use of an external electromagnet requires that the infant be placed in a specially constructed bed having a large annular electromagnet. In addition to the expense associated with providing such a bed, the electromagnet itself can significantly impact the ability of caregivers to nurture the infant. The use of an external electromagnet also requires a subsequent procedure to surgically join the esophageal sacs into a continuous lumen. Surgically joining the esophageal sacs requires great surgical skill, and can present significant operative and post-operative complications. For example, surgical joining can result in the misalignment of the esophagus, and consequently, difficulty swallowing. Additional complications include gastroesophageal reflux, which can lead to ulcers in the lower part of the esophagus.

Applying traction through surgically placed sutures also presents several drawbacks. The main drawback of using sutures is the need for a significant surgical procedure once the esophageal sacs are sufficiently lengthened by the traction. This procedure involves surgically joining the esophageal sacs, which can result in a number of the complications detailed above. Moreover, as the sutures draw the esophageal sacs together, the sutures frequently tear out of one or both of the sacs. This requires at least one, and often multiple additional surgeries to re-suture the esophageal sacs. Additionally, if the approximation of the esophageal sacs occurs too quickly, the esophageal tissue may not regenerate at the required rate or the passageway formed between the esophageal sacs may be irregular, potentially leading to blockage of the passageway.

Accordingly, in view of the drawbacks of current technology, there is a desire for a system and a method for approximating the esophageal sacs of an infant afflicted with esophageal atresia and forming an open passageway between the two esophageal sacs.

BRIEF SUMMARY

Accordingly, it is an object of the present invention to provide a system and a method having features that resolve or improve on one or more of the above-described drawbacks.

The foregoing object is obtained by providing a medical system and a method for joining an upper esophageal sac and a lower esophageal sac in an infant. The medical system includes a first elongate member having a proximal end, a distal end and a first magnet operably connected to the distal end, the first magnet including an end portion configured to abut an interior surface of the upper esophageal sac. The medical system also includes a second elongate member having a proximal end, a distal end, and a second magnet operably connected to the distal end, the second magnet including an end portion configured to abut an interior surface of the lower esophageal sac. The medical system further includes a third elongate member having a proximal end, a distal end, a third magnet operably connected to the distal end and a spacer positioned distal to the third magnet. The third magnet includes an end portion, the spacer having a first end portion operatively abutting the third magnet end portion of the third elongate member and a second end portion configured to abut the interior surface of the upper esophageal sac. The third elongate member is positionable in the upper esophageal sac after the first elongate member has been removed from the upper esophageal sac. A magnetic force between the first magnet of the first elongate member and the second magnet of the second elongate member is configured to pull the first magnet and the second magnet towards each other to lengthen the upper and lower esophageal sacs.

BRIEF DESCRIPTION OF THE DRAWINGS

FIG. 1 is a side view of an embodiment of a first esophageal catheter in accordance with the present invention;

FIG. 2 is a side view of an embodiment of a gastric catheter;

FIG. 3 is a side view of an embodiment of a second esophageal catheter;

FIG. 10 is a view of one embodiment of the first esophageal catheter and the gastric catheter positioned within an infant;

FIG. 11 is a view of one embodiment of the first esophageal catheter and the gastric catheter positioned within the infant with the esophageal sacs growing closer together;

DETAILED DESCRIPTION

Figure 6:
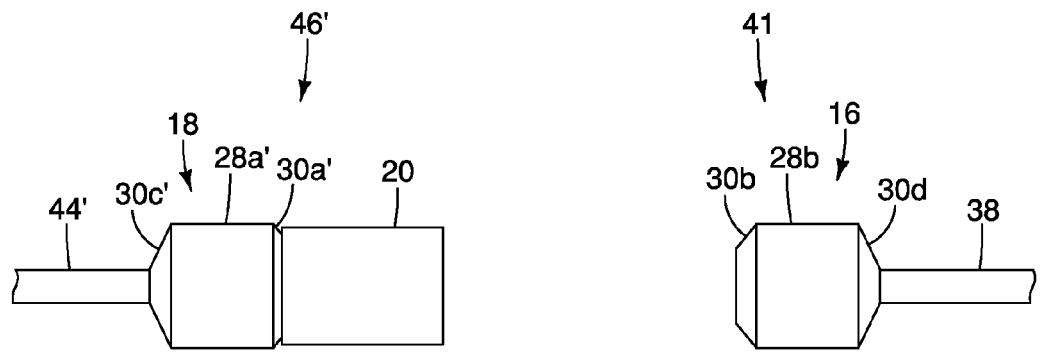
FIG. 6 is a partial side view of the second esophageal catheter and the gastric catheter in a first position.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly. Additionally, it should be noted that, as used herein, the term "magnet" refers to a material that is naturally surrounded by a magnetic field and has the property of attracting iron or steel.

As used in the specification, the terms proximal and distal should be understood as being in the terms of a physician delivering the stent to a patient. Hence the term "distal" means the portion of the device that is farthest from the physician and the term "proximal" means the portion of the device that is nearest to the physician.

FIGS. 1-3 illustrate an embodiment of a system 10 in accordance with the present invention. The system 10 may be used to correct esophageal atresia in an infant. The system 10 includes a first esophageal catheter 14, a gastric catheter 16 and a second esophageal catheter 18. The first and second esophageal catheters 14, 18 may be the same catheter or a different catheter where the second catheter 18 additionally includes a spacer 20 as explained in more detail below.

As shown in FIG. 1, the esophageal catheter 14 includes an elongate, tubular sheath 32 having a distal end portion 52 and a proximal end portion 64. The esophageal catheter 14 also may include at least two lumens 33, 35 extending longitudinally therethrough. The first lumen 33 extends from ports 54, which are located at the distal end 52, to a proximal port 58 for removing fluids that collect within the upper esophageal sac. In use, suction can be applied to the proximal port 58 to remove any fluid or mucous that collects within the upper esophageal sac while the catheters 14 is in position within the upper esophageal sac. The second lumen 35 is sized to slidably accept a catheter 44 that is distally extendable from the sheath 32. The catheter 44 may be provided with a flared distal tip 48 and a lumen 23 sized to accept a standard wire guide 98, such as a 0.025" METRO™ Wire Guide (Cook Medical Incorporated, Bloomington, Ind.).

As illustrated in FIG. 1, a first magnet 28a may be fixed to a distal portion 46 of the catheter 44. The first esophageal catheter 14 may be configured to pass the first magnet 28a through the esophagus and into abutment with the terminus of the upper esophageal sac. The first magnet 28a may be fixed to the catheter 44 using any technique known to one skilled in the art, for example by gluing, bonding, welding, and/or positioning the magnet 28a between the flared distal tip 48 and a band 50 (See FIG. 1). In some embodiments, a stylet 101 may be provided at least partially within the catheter 44 for increasing the rigidity of the catheter 44 when the catheter 44 is delivered to the upper esophageal sac. In some embodiments, the stylet 101 may be removed from the catheter 44 after the catheter 44 is placed within the patient.

Figure 8:
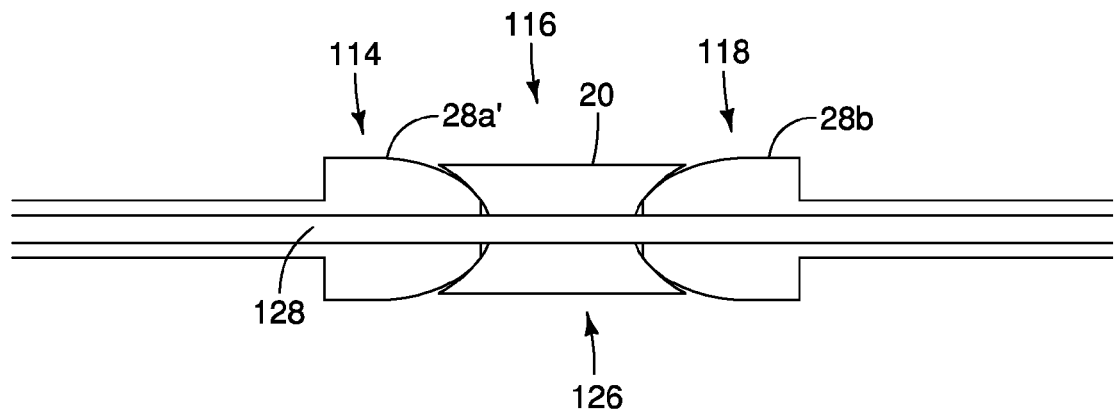
FIG. 8 is a partial sectional view of the second esophageal catheter, the spacer and the gastric catheter in the second position.

FIG. 2 illustrates an embodiment of the gastric catheter 16 of the system 10. The gastric catheter 16 includes a tubular sheath 36 having a distal end portion 45 and a proximal end portion 47. The gastric catheter 16 may also include a first lumen 51, a second lumen 55, and a third lumen 59 that are accessible via hub connectors 53, 56, 60, respectively. The first lumen 51 is adapted to inflate a balloon 70 of the gastric catheter 16. The first lumen 51 extends between an inflation port 82, located on the sheath 36 and positioned inside the balloon 70, and an inflation port 84 at the hub connector 53. As shown in FIG. 8, the balloon 70 may be used in conjunction with a bolster 78 provided on the sheath 36 to securely fit the gastric catheter 18 to the stomach wall and to prevent any leaking of gastric contents outside of the stomach. The gastric catheter 16 may also include a feeding tube 85 extending from a proximal port 86 to a distal port 74. The feeding tube 85 is adapted to deliver nutrients to an infant's stomach via the distal port 74 and, additionally, if necessary, medications or other fluids may also be delivered to the infant's stomach through the feeding tube 85.

As shown in FIG. 2, the gastric catheter 16 may further include the third lumen 59 that may be sized to slidably accept a catheter 38. The catheter 38 is similar to the catheter 44 in that it may include a flared distal tip 49 and a lumen 25 sized to accept a standard wire guide 97, such as a 0.025" METRO™ Wire Guide (Cook Medical Incorporated, Bloomington, Ind.).

In an embodiment of the gastric catheter 16, a second magnet 28b is fixed to a distal portion 41 of the catheter 38. The gastric catheter 16 may be configured to pass the second magnet 28b into abutment with the terminus of the lower esophageal sac. The second magnet 28b may be fixed to the catheter 38 using any technique known to one skilled in the art, for example by gluing, bonding, welding, and/or positioning the magnet 28b between the flared distal tip 49 and a band 50 (See FIG. 2). In some embodiments, a stylet 102 may be provided at least partially within the catheter 38 for increasing the rigidity of the catheter 38 when the catheter 38 is delivered to the lower esophageal sac. In some embodiments, the stylet 102 may be removed from the catheter 38 after the catheter 38 is placed within the patient. When the first and second magnets 28a, 28b are in place, both magnets 28a, 28b are approximated by their magnetic force, thereby imparting a constant traction upon the esophageal sacs. Additionally, the first and second magnets 28a, 28b are configured so that the approximating force therebetween properly aligns the magnets and the esophageal sacs.

The system 10 further includes the second esophageal catheter 18 as shown in FIG. 3. The first and second esophageal catheters 14, 18 and the components thereof will be described herein as being two different catheters having similar components. However, one skilled in the art will understand that the first esophageal catheter 14 and the components thereof may also be used as the second esophageal catheter with the spacer 20 added to the first esophageal catheter 14. Both the first and second esophageal catheters 14, 18 are configured for placement in an upper esophageal sac where the second esophageal catheter 18 is positionable in the upper esophageal sac after the first esophageal catheter 14 has been positioned in the upper esophageal sac for a period of time and then removed as explained in more detail below.

Similar to the first esophageal catheter 14, the second esophageal catheter 18 also includes an elongate, tubular sheath 32' having a distal end portion 52' and a proximal end portion 64' and at least two lumens 33', 35' extending longitudinally therethrough as shown in FIG. 3. Ports 54', which are located at the distal end 52' and a proximal port 58' may be used for suction for removing fluids that collect within the upper esophageal sac as described above. The second lumen 35' of the second esophageal catheter 18 is sized to slidably accept a catheter 44' that is distally extendable from the sheath 32'. The catheter 44' may be provided with a flared distal tip 48' (not shown) and a lumen 23' sized to accept a standard wire guide 98', such as a 0.025" METRO™ Wire Guide (Cook Medical Incorporated, Bloomington, Ind.).

As illustrated in FIG. 3, a third magnet 28a' may be fixed to a distal portion 46' of the catheter 44' and the spacer 20 positioned distal to the third magnet 28a'. The second esophageal catheter 18 may be configured to pass the spacer 20 and the third magnet 28a' through the esophagus so that the spacer 20 is in abutment with the terminus of the upper esophageal sac after the first catheter 14 has been removed. The upper magnet 28a' may be fixed to the catheter 44' using any technique known to one skilled in the art, for example by gluing, bonding, welding, and/or positioning the magnet 28a' between the flared distal tip 48' and a band 50' (See FIG. 1). In some embodiments, a stylet 101' may be provided at least partially within the catheter 44' for increasing the rigidity of the catheter 44' when the catheter 44' is delivered to the upper esophageal sac. In some embodiments, the stylet 101' may be removed from the catheter 44' after the catheter 44' is placed within the patient.

Figure 4:
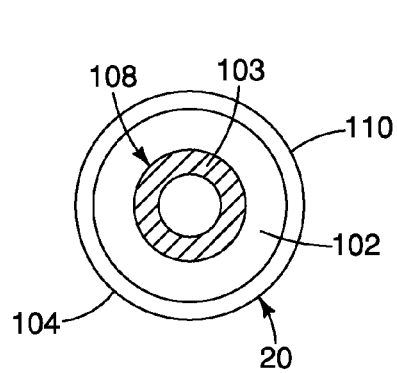
FIG. 4 is an end view of an embodiment of a spacer in accordance with the present invention.
Figure 5:
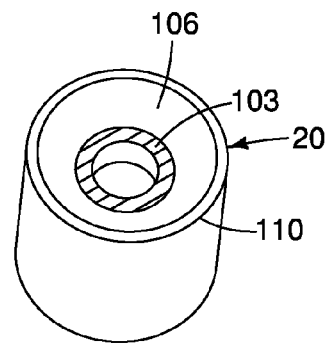
FIG. 5 is a perspective view of the spacer shown in FIG. 4.

As shown in FIGS. 3 and 6, the second esophageal catheter 18 includes the spacer 20 positioned distal to the magnet 28a'. FIGS. 4 and 5 illustrate an embodiment of the spacer 20 of the second esophageal catheter 18 of the system 10. As shown in FIG. 4, the spacer 20 may be cylindrically shaped. Other shapes for the spacer 20 are also possible, however, a smooth outer surface 102 is preferred to allow the formation of a uniform lumen between the upper and lower esophageal sacs once the anastomosis of the esophageal sacs is complete. The spacer 20 also includes a lumen 103 extending therethrough. The spacer 20 may be formed with a first end 104 having a flat surface as shown in FIG. 4 and a second end 106 having a concave surface configured to mate with the end 30b of the second magnet 28b. In some embodiments, both ends 104, 106 may include flat or concave surfaces or the first end 104 may have a concave surface and the second end 106 may have a flat surface. In some embodiments, the spacer 20 may be formed from two materials as shown in FIG. 4. The spacer 20 may be formed with an inner core 108 and an outer portion 110 at least partially surrounding the inner core 108. By way of non-limiting example, the inner core 108 may be formed from 416 stainless steel and the outer portion 110 may be formed from 303 stainless steel. The 416 stainless steel is ferromagnetic while the 303 stainless steel is not magnetic or much less magnetic. Other materials may also be used to form the spacer. Advantageously, forming the inner core 108 from a magnetic material and the outer portion 110 from a less magnetic material relative to the inner core facilitates proper self-alignment when third magnet 28a', the spacer 20 and the second magnet 28b of the gastric catheter 16 mate. The spacer 20 having the outer portion 110 formed from a less magnetic material also helps to avoid difficulties forming concave shapes in magnetic material, for example when the concave shape makes the magnet too brittle to be useful. In some embodiments, the spacer 20 may have a length that is similar to the third magnet 28a' and in some embodiments, the spacer 20 may be longer or shorter than the third magnet 28a'. The length of the space 20 may depend on the rate of growth of the tissue and may be varied as the ends of the bodily lumens move closer together.

Figure 7:
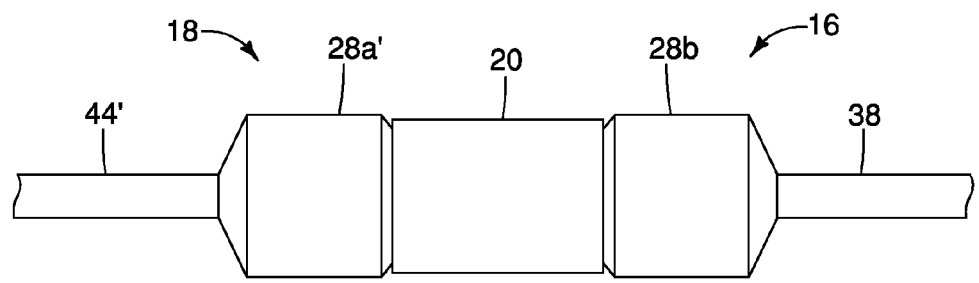
FIG. 7 is a partial side view of the second esophageal catheter and the gastric catheter in a second position.
Figure 9:
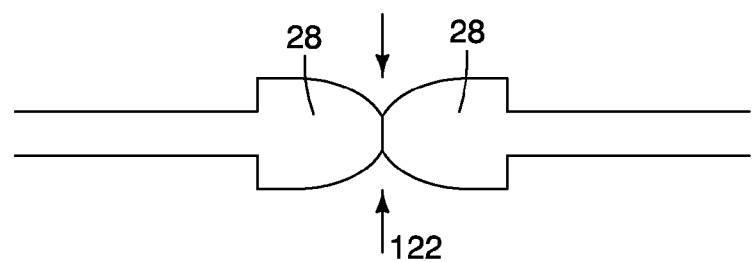
FIG. 9 is a partial view of two magnets mating and the recess formed where the two magnets meet.

As shown in FIGS. 7 and 8, the third magnet 28a', the spacer 20 and the second magnet 28b have similar outer diameters 114, 116, 118, respectively. The similar outer diameters 114, 116, 118 allow the lumen that is formed between the upper and lower esophageal sacs when the upper and lower esophageal sacs join to be larger and more uniform than if formed by two magnets alone. Compare FIGS. 8 and 9, illustrating the more uniform outer surface in FIG. 8 and a narrowed outer surface 122 shown at the arrows in FIG. 9 when two magnets 28 alone mate. The narrowed outer surface 122 creates a stricture in the newly joined upper and lower esophageal sacs that may require later stenting or dilation as described below. In addition, the spacer 20 allows for slower approximation and more time for tissue regeneration of the upper and lower esophageal sacs when compared to the approximation rate for two magnets 28 alone. Without the spacer 20, as the magnets 28 approach each other the force between the magnets 28 increases exponentially. As the magnets 28 approach each other and the attraction forces are higher, the tissue in the upper and lower esophageal sacs may not be able to regenerate when the magnets reach a certain proximity. The force of the attraction between the magnets 28 may exceed the tissue regeneration capacity once the magnets 28 are within a certain vicinity of each other. The spacer 20 reduces the force of the attraction between the magnets 28 to allow for time for the tissue to properly regenerate.

It should be noted that the magnets 28a, 28a', 28b can be provided in a variety of shapes. For example, the magnets 28a, 28a', 28b may include atraumatic distal ends 30a, 30a', 30b, respectively, as shown in FIGS. 4 and 5 so that the tissue in the upper and lower esophageal sacs is not damaged as the magnetic forces attract the magnets 28a, 28a', 28b closer together and the upper and lower esophageal sacs elongate toward each other. The distal ends 30a, 30b may be curvilinear, including rounded, oblong, bullet shaped and the like. Other shapes for the distal ends 30a, 30a', 30b are also possible. Proximal ends 30c, 30c', 30d of the magnets 28a, 28a', 28b may also be curvilinear. In some embodiments, the proximal ends 30c, 30c', 30d may be flattened or blunt. The first magnet 28a may include a passageway 26 therethrough and the second magnet 28b may include a passageway 27 therethrough so that the magnets 28a, 28b may be positioned using the wireguides 98, 97 respectively. Similarly, the third magnet 28a' may include a passageway 26' therethrough and the magnets 28a', 28b may be positioned using the wireguides 98', 97 respectively. As shown in FIG. 8, the third magnet 28a', the spacer 20 and the second magnet 28b can be shaped so as to nest and/or create substantially smooth outer surface 126 and a continuous passageway 128 between catheter 44' and catheter 38. The passageway 26' of the third magnet 28a', the lumen 103 of the spacer 20 and the passageway 27 of the second magnet 28b align to form the continuous passageway 128 once the upper and lower esophageal sacs have joined and the tissue at the ends of the esophageal sacs has necrosed between the spacer 20 and the second magnet 28b. This continuous passageway 128 allows the insertion of a guide wire from the proximal hub assembly 96 through both the gastric catheter 16 and the second esophageal catheter 18. In some embodiments, the third magnet 28a', the second magnet 28b and the spacer 20 are self-aligning to form the continuous passageway 128. As a result, once communication is established between both catheters (as detailed below), a wire guide can be used to secure the esophageal lumen between the stomach and the mouth of the infant.

The magnetic elements may be formed from any material having magnetically attractable materials. As used herein, magnetic refers to all magnetically attractable materials, such as magnets and magnetically charged members, as well as ferrous materials such as iron, nickel cobalt, steel and various alloys that are attractable to a magnet. For example the magnets may be rare-earth magnets, such as Neodymium-iron-boron, cobalt, etc. Although the first and second magnetic elements have been depicted as magnets, it will be recognized by one skilled in the art that only one of the magnetic elements may be a magnet where the other magnetic element is a ferrous material or other material that is simply attracted to the one magnet. The magnetic elements may also include a protective coating to protect the magnetic elements from the potentially corrosive effects of the bodily fluids. By way of non-limiting example, the magnetic elements may be coated with a polymeric coating such as parylene, polyesters, polyurethanes, polyethylenes, polyamides, and silicone. The coating may also be formed of various metals or alloys, such as TEFLON® and PARALENE® and the like.

The shafts of the esophageal catheters 14, 18 are preferably formed of a biocompatible polymer having a smooth outer surface. In some embodiments, the radius of the shaft may be approximately 10 French, so as to allow relatively effortless passage into the esophagus of an infant. The materials used to form the shafts may be any material, including but not limited to polyamides, polyurethanes, nylons, polyethylenes, including high-density polyethylene (HDPE), polyether block amide (PEBA) which is available as Pebax®, polyester (PET), polyetheretherketone (PEEK) or PERT. The gastric catheter 16 may also be formed of similar materials. In some embodiments, the catheters 38, 44 and 44' may be formed from suitably flexible materials for insertion into the infant's esophageal sacs and positioning therein as the esophageal sacs elongate. Suitable materials include, but are not limited to polyamides, polyurethanes, nylons, polyethylenes, including high-density polyethylene (HDPE), polyether block amide (PEBA) which is available as Pebax®, polyester (PET), polyetheretherketone (PEEK).

FIGS. 10-13 depict the illustrative esophageal and gastric catheters being used to approximate the upper and lower esophageal sacs of an infant. First, as shown in FIG. 10, a gastrostomy is performed on the infant and the gastric catheter 16 is inserted into the infant's stomach. This procedure is performed using standard fluoroscopic techniques. The gastric catheter 16 should be inserted until a bolster 78 abuts the infant's abdomen. At this point in the procedure, a contrast fluid (e.g., Barrium) is injected through the port 84 and into the balloon 70. This causes the balloon 70 to expand, thereby securing the gastric catheter 16 to the stomach wall, as illustrated in FIG. 10. After the gastric catheter 16 is in place and secured, the catheter 38 is advanced distally through the stomach, beyond the lower esophageal sphincter, and into the lower esophageal sac. When properly in place, the second magnet 28b abuts the terminus of the lower esophageal sac.

Once the second magnet 28b is situated adjacent the terminus of the lower esophageal sac, the first esophageal catheter 14 may be inserted. As illustrated in FIG. 10, the first esophageal catheter 14 is advanced into the mouth of the infant and distally down the lumen of the upper esophageal sac. Alternatively, the first esophageal catheter 14 can be advanced through the infant's nasal passage. In either case, the first magnet 28a is advanced until it abuts the terminus of the upper esophageal sac. At this point, the first magnet 28a can be attracted by the second magnet 28b, thereby providing traction forces and aligning the esophageal sacs.

Figure 13:
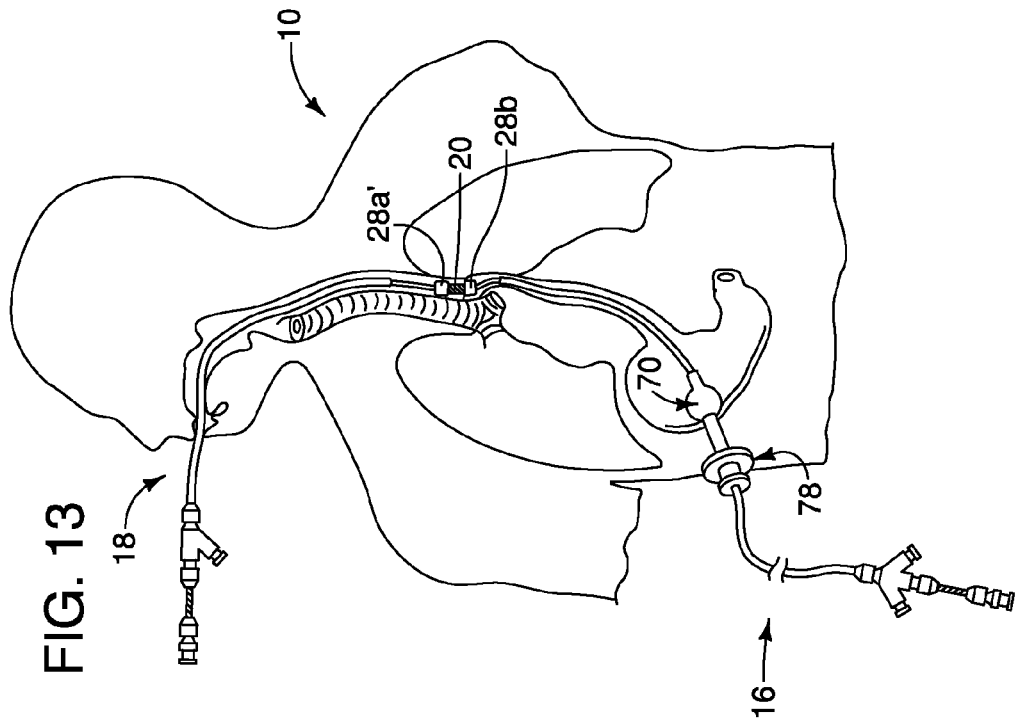
FIG. 13 is a view of the second esophageal catheter and the gastric catheter positioned within the infant.
Figure 12:
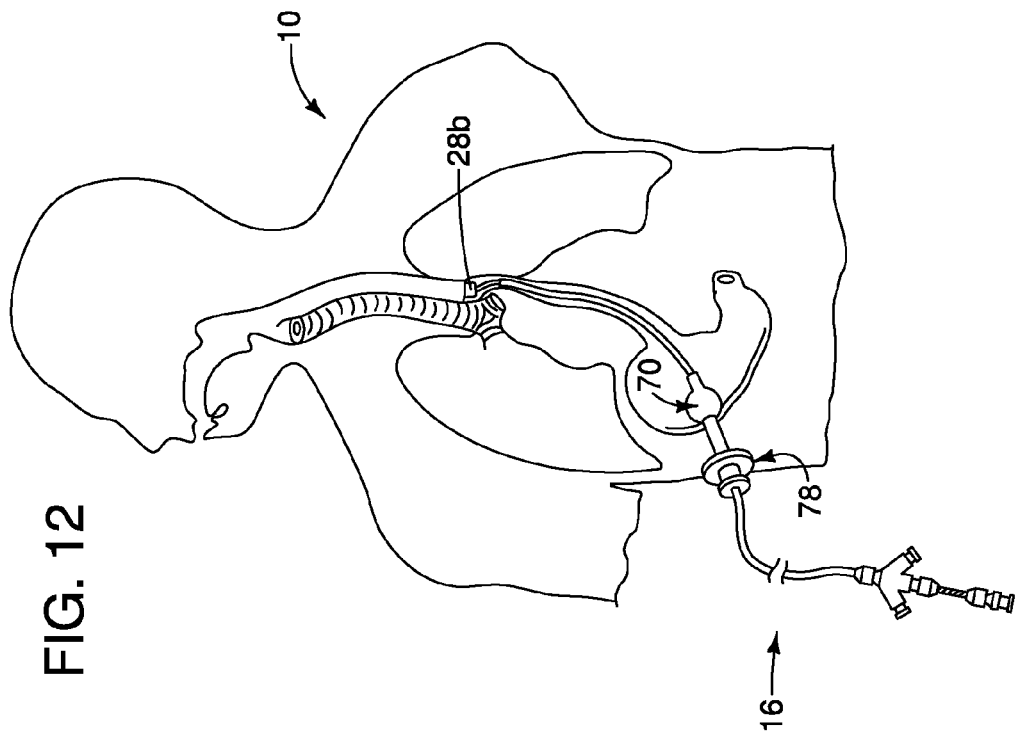
FIG. 12 is a view of the first esophageal catheter withdrawn from the infant.

Over a period of about 3 to 7 days, the first and second magnets 28a, 28b are attracted toward each other and the upper and lower esophageal sacs elongate. As the first and second magnets 28a, 28b get closer together, the attractive force increases. In order to allow enough time for new tissue to generate in the upper and lower esophageal sacs, the first esophageal catheter 14 is withdrawn from the upper esophageal sac as shown in FIG. 12. The second esophageal catheter 18 including the spacer 20 is positioned in place of the first esophageal catheter 14 with the spacer 20 abutting the terminus of the upper esophageal sac as shown in FIG. 13. The spacer 20 still allows the traction force between the third and second magnets 28a', 28b to pull the upper and lower esophageal sacs towards each other, but the rate is reduced with the spacer 20 so the tissue has sufficient time to regenerate. The physician may withdraw the first esophageal catheter 14 and replace the first esophageal catheter 14 with the second esophageal catheter 18 when the distance between the first and second magnets 28a, 28b is about 2-8 mm. In some embodiments, the physician may withdraw the first esophageal catheter 14 and replace the first esophageal catheter 14 with the second esophageal catheter 18 when the distance between the first and second magnets 28a, 28b is about 5-6 mm. Other distances between the first and second magnets 28a, 28b may be used as to determine when the first esophageal catheter 14 is replaced with the second esophageal catheter 18. The time of the exchange of the first and second esophageal catheters 14, 18 may be based on such factors as the rate of growth of the upper and lower esophageal sacs, the original distance between the upper and lower esophageal sacs, and the like. The traction caused by the third and second magnets 28a', 28b will cause the esophageal sacs to approximate and subsequently physically join together so as to form a continuous esophageal passageway. The constant magnetic force created by the magnets 28a', 28b and the spacer 20 initially causes the esophageal sacs to grow together and causes pressure-induced necrosis of the esophageal sacs between the spacer 20 and the second magnet 28b. The continuation of the pressure-induced necrosis along with the rapid growth ultimately results in the formation of a continuous lumen from the mouth to the stomach. As noted above, the third and second magnets 28a', 28b and the spacer 20 are configured to align and connect with each other so as to create a continuous passageway from the catheter 44 to the catheter 38.

At this point in the procedure, a single guide wire is delivered through the continuous passageway formed by catheters 44 and 38. Thereafter, the esophageal and gastric catheters can be removed from the infant. A feeding tube is then placed over the guide wire and the guide wire is removed.

After the procedure is complete, the infant should be periodically observed for any signs of re-synopsis. If any re-synopsis is observed, a balloon catheter can be used to perform an esophageal dilation. In addition to esophageal dilation, a stent or stent-graft can be placed within the esophagus in the area of the synopsis. Alternatively, a stent or stent graft can be used to prevent any such re-synopsis.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A medical system for joining an upper esophageal sac and a lower esophageal sac in an infant, the medical system comprising:
   a first elongate member comprising a proximal end, a distal end and a first magnet operably connected to the distal end, the first magnet comprising an end portion configured to abut an interior surface of the upper esophageal sac;
   a second elongate member comprising a proximal end, a distal end, and a second magnet operably connected to the distal end, the second magnet comprising an end portion configured to abut an interior surface of the lower esophageal sac;
   a third elongate member comprising a proximal end, a distal end, a third magnet operably connected to the distal end and a spacer positioned distal to the third magnet, the third magnet comprising an end portion, the spacer comprising a first end portion operatively abutting the third magnet end portion of the third elongate member so that the third magnet is positioned between the distal end of the third elongate member and the first end portion of the spacer and the spacer comprising a second end portion configured to abut the interior surface of the upper esophageal sac; the third elongate member positionable in the upper esophageal sac after the first elongate member has been removed from the upper esophageal sac; and
   wherein a magnetic force between the first magnet of the first elongate member and the second magnet of the second elongate member is configured to pull the first magnet and the second magnet towards each other to lengthen the upper and lower esophageal sacs.

2. The medical system of claim 1, wherein the third magnet of the third elongate member comprises a third magnet passageway therethrough.

3. The medical system of claim 2, wherein the spacer comprises a passageway therethrough.

4. The medical system of claim 3, wherein the second magnet comprises a second magnet passageway therethrough and the third magnet passageway, the second magnet passageway and the spacer passageway operably connect to form a substantially continuous passageway when the upper and lower esophageal sacs are joined.

5. The medical system of claim 1, wherein the spacer comprises two different materials.

6. The medical system of claim 1, further comprising a guide wire, the guide wire extendable through a continuous passageway formed through the second magnet, the spacer and the third magnet when the upper and lower esophageal sacs are connected.

7. The medical system of claim 1, wherein the third magnet of the third elongate member comprises a third magnet passageway therethrough.

8. The medical system of claim 7, wherein the spacer comprises a passageway therethrough.

9. The medical system of claim 8, wherein the second magnet comprises a second magnet passageway therethrough and the third magnet passageway, the second magnet passageway and the spacer passageway operably connect to form a substantially continuous passageway when the first and second body lumens are joined.

10. A medical system for joining first body lumen and a second body lumen in a patient, the medical system comprising:
    a first elongate member comprising a proximal end, a distal end and a first magnet operably connected to the distal end, the first magnet comprising an end portion configured to abut an interior surface of the first body lumen;
    a second elongate member comprising a proximal end, a distal end, and a second magnet operably connected to the distal end, the second magnet comprising an end portion configured to abut an interior surface of the second body lumen;
    a third elongate member comprising a proximal end, a distal end, a third magnet operably connected to the distal end and a spacer positioned distal to the third magnet, the third magnet comprising an end portion, the spacer comprising a first end portion operatively abutting the third magnet end portion of the third elongate member so that the third magnet is positioned between the distal end of the third elongate member and the first end portion of the spacer and the spacer comprising a second end portion configured to abut the interior surface of the first body lumen; the third elongate member positionable in the first body lumen after the first elongate member has been removed from the first body lumen; and
    wherein a magnetic force between the first magnet of the first elongate member and the second magnet of the second elongate member is configured to pull the first magnet and the second magnet towards each other to lengthen the first and second body lumens.

11. The medical system of claim 10, wherein the spacer comprises an inner core having a passageway formed therethrough and an outer portion at least partially surrounding the inner core.

12. The medical system of claim 11, wherein the outer portion comprises a less magnetic material relative to the inner core.

13. The medical system of claim 10, wherein the second magnet, the spacer and the third magnet are self-aligning.

14. The medical system of claim 10, wherein the first, second and third magnets comprise atruamatic distal ends.

15. The medical system of claim 10, wherein the spacer comprises a concave second end configured to mate with the distal end of the second magnet.

16. The medical system of claim 10, further comprising a first outer sheath having an outer sheath lumen extending at least partially therethrough, at least a portion of the first elongate member movably positionable within the outer sheath lumen.

17. The medical system of claim 16, wherein the first outer sheath further comprises a plurality ports operably connected to the lumen.

18. The medical system of claim 10, further comprising a second outer sheath having a lumen extending at least partially therethrough, at least a portion of the second elongate member movably positionable within the lumen.

19. The medical system of claim 18, wherein the second outer sheath further comprises a balloon.

20. The medical system of claim 10, wherein the spacer comprises two different materials.

* * * * *